US010363150B1

(12) United States Patent
Braun et al.

(10) Patent No.: US 10,363,150 B1
(45) Date of Patent: Jul. 30, 2019

(54) PROSTHETIC DEVICE WITH A ROTATABLE PYRAMID AND LATERAL TRAVEL LIMIT

(71) Applicant: American Prosthetic Components, LLC, Green Bay, WI (US)

(72) Inventors: Jeffrey Robert Braun, Richfield, WI (US); Erin Jeanne Ballast, Green Bay, WI (US)

(73) Assignee: American Prosthetic Components, LLC, Green Bay, WI (US)

( * ) Notice: Subject to any disclaimer, the term of this patent is extended or adjusted under 35 U.S.C. 154(b) by 0 days.

(21) Appl. No.: 15/470,745

(22) Filed: Mar. 27, 2017

Related U.S. Application Data

(60) Provisional application No. 62/314,916, filed on Mar. 29, 2016.

(51) Int. Cl.
*A61F 2/62* (2006.01)
*A61B 5/02* (2006.01)
(Continued)

(52) U.S. Cl.
CPC ............. *A61F 2/76* (2013.01); *A61F 2/601* (2013.01); *F16B 5/0052* (2013.01);
(Continued)

(58) Field of Classification Search
CPC ...... A61F 2002/5018; A61F 2002/5021; A61F 2002/5023; Y10T 403/32147;
(Continued)

(56) References Cited

U.S. PATENT DOCUMENTS 5,425,782 A  6/1995 Phillips
5,443,526 A  8/1995 Hoerner
(Continued)

FOREIGN PATENT DOCUMENTS

GB    2 162 069 A  * 1/1986  ............... A61F 2/62
WO   WO 97/17042 A1 * 5/1997  ............... A61F 2/62

OTHER PUBLICATIONS

Prosthetic Design, Inc., Stealth360TM, PYR-SL-CF Pyramid: Sliding or Rotating Product Information, Circa 2015 (Applicant discovered it on Aug. 3, 2015. The actual date of publication is both unknown and not relevant as the literature shows products described in U.S. Pat. Nos. 6,033,440 and 6,231,618, both of which are sufficiently earlier than the effective U.S. filing date and any foreign priority date of the present application so that the particular month and year of publication is not an issue), 1 page.

*Primary Examiner* — David H Willse
(74) *Attorney, Agent, or Firm* — Brannen Law Office, LLC

(57) ABSTRACT

A prosthetic device having a rotatable pyramid and lateral travel limit is provided. A first member has a first end connectable to a prosthetic component and a second end with a bar having sides and a distal face. The distal face has ribs thereon. A central hole is provided through the first member. A second member has a first end with a pyramid and a second end with a ring that defines a recess with a solid face. A third member has a dome on a first end and a channel on the second end. The pyramid extends through a central hole through the dome. A screw passes through the central hole of the first member wherein it can engage the second member within the recess. The lateral movement of the bar within the channel is bound by the screw contacting the second member.

11 Claims, 12 Drawing Sheets

(51) Int. Cl.
*A61F 2/76* (2006.01)
*A61F 2/60* (2006.01)
*F16B 5/00* (2006.01)
*F16B 5/02* (2006.01)
*A61F 2/50* (2006.01)

(52) U.S. Cl.
CPC ...... *F16B 5/0225* (2013.01); *A61F 2002/502* (2013.01); *A61F 2002/5016* (2013.01); *A61F 2002/5018* (2013.01); *A61F 2002/5021* (2013.01); *A61F 2002/5023* (2013.01); *A61F 2002/5083* (2013.01); *F16B 2200/30* (2018.08); *Y10T 403/32147* (2015.01); *Y10T 403/32229* (2015.01); *Y10T 403/7041* (2015.01); *Y10T 403/7073* (2015.01)

(58) Field of Classification Search
CPC ....... Y10T 403/32229; Y10T 403/7073; F16B 5/0052; F16B 5/0225; F16B 5/0032; F16B 2200/30

USPC ............................................. 623/38; 403/381
See application file for complete search history.

(56) References Cited

U.S. PATENT DOCUMENTS

| | | | |
|---|---|---|---|
| 5,888,233 | A | 3/1999 | Randstrom |
| 6,013,105 | A | 1/2000 | Potts |
| 6,033,440 | A | 3/2000 | Schall et al. |
| 6,231,618 | B1 | 5/2001 | Schall et al. |
| 7,166,132 | B2 | 1/2007 | Callaway et al. |
| 7,338,532 | B2 | 3/2008 | Haberman et al. |
| D733,884 | S | 7/2015 | Hillmann et al. |
| 2004/0059433 | A1 | 3/2004 | Slemker et al. |
| 2005/0027371 | A1 | 2/2005 | Chen |
| 2010/0036506 | A1* | 2/2010 | Wang ........................ A61F 2/60 623/38 |
| 2014/0074254 | A1 | 3/2014 | Curtis |

* cited by examiner

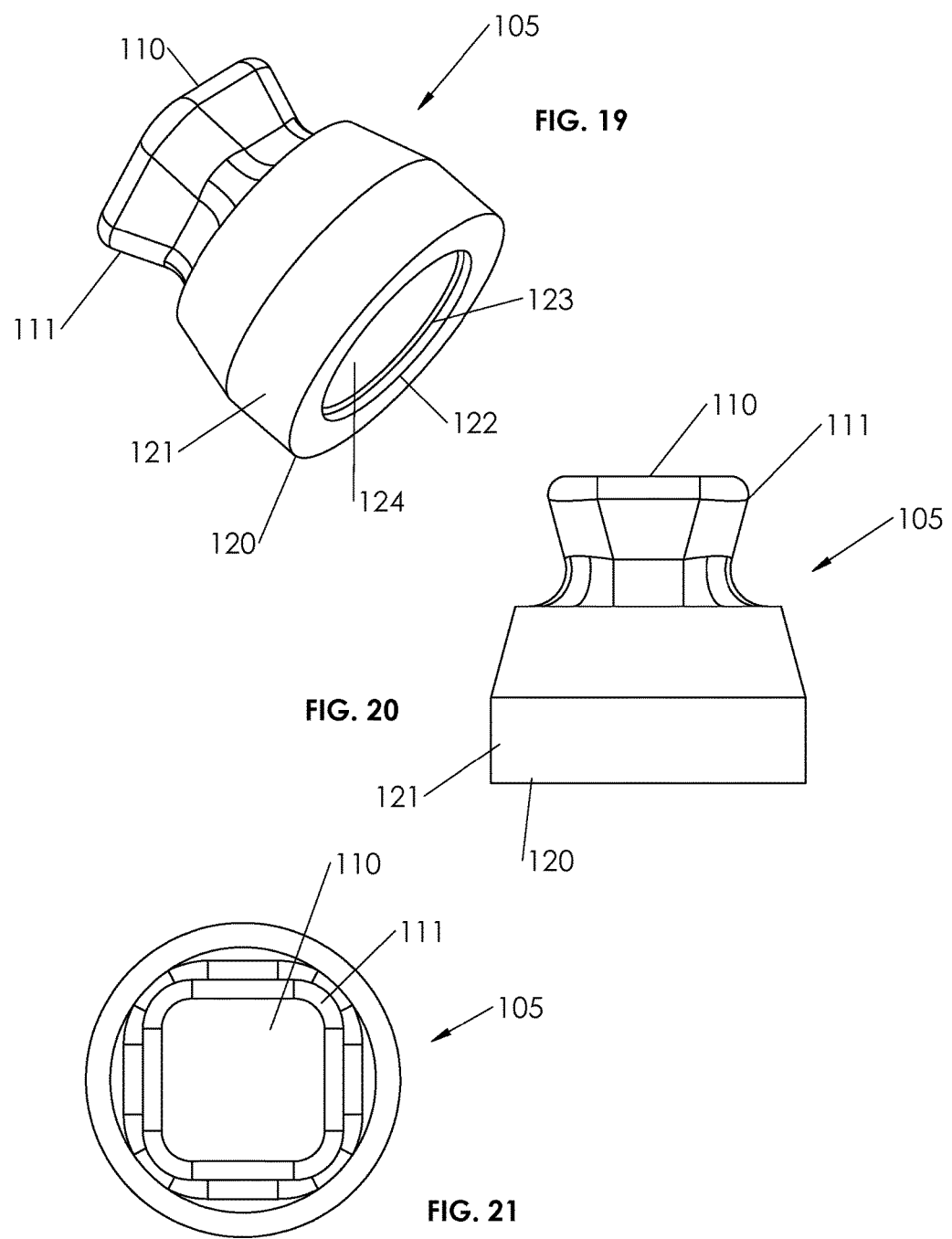

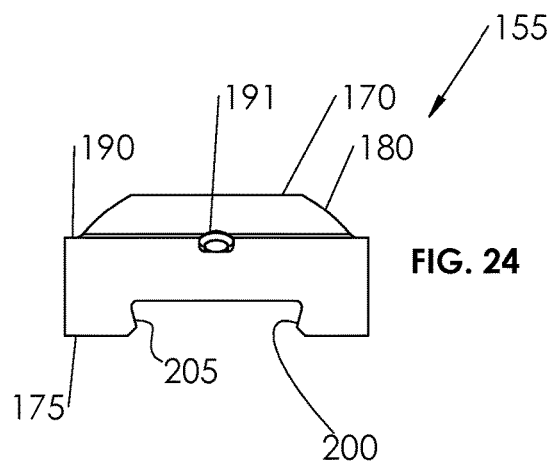
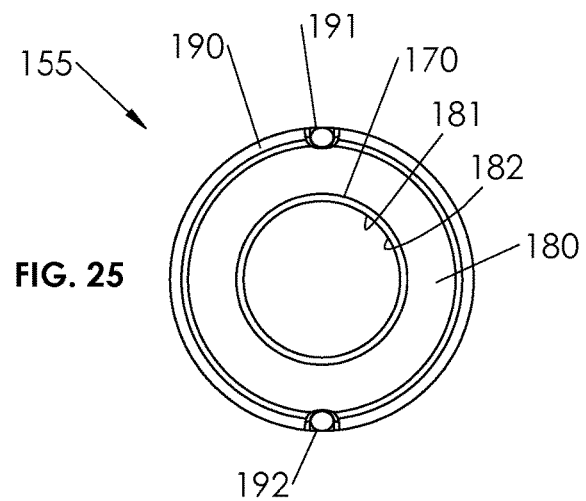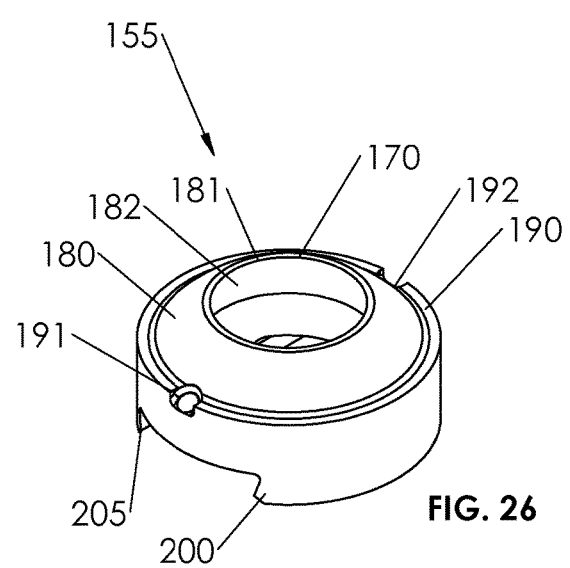

PROSTHETIC DEVICE WITH A ROTATABLE PYRAMID AND LATERAL TRAVEL LIMIT

This patent application claims priority on and the benefit of provisional application 62/314,916 filed Mar. 29, 2016, the entire contents of which are hereby incorporated herein by reference.

BACKGROUND OF THE INVENTION

1. Field of the Invention

The present invention relates to a prosthetic device and in particular to a prosthetic device having a rotatable pyramid and lateral travel limit.

2. Description of the Related Art

Many prosthetic devices exist having some degree of adjustability. Of the many existing devices, some are described in the following patents and published applications:

United States Patent Number ("USPN") D733,884 to Hillmann et al. is titled Adjustable Adapter, and shows an ornamental design thereof.

U.S. Pat. No. 5,425,782 to Phillips is titled Alignment Fixture for Prosthetic Device. It shows a fixture permitting adjustment of the position and axial alignment of a prosthesis is characterized by a first attachment member associated with a socket attached to the wearer's stump, and by the fixture's ability to be adjusted without the necessity of removing the socket from the wearer's stump. A second attachment member is operatively attached to the prosthesis, and adjustable attachment means operatively connects the second attachment member to the first attachment member. The adjustable attachment means includes a central bolt member which may be accessed for adjustment without removing the socket from the wearer. The bolt member preferably extends through a rectilinear central opening in the first attachment member, providing a range of selectable lateral positions of the second attachment member with respect to the first attachment member. The adjustable attachment means also preferably includes a frustoconical member disposed between the first and second attachment members, and auxiliary adjustment members operatively engaged between the second attachment member and the frustoconical member to permit the axial alignment of the second attachment member to be adjusted with respect to the first attachment member.

U.S. Pat. No. 5,443,526 to Hoerner is titled Adjustable Prosthetic Connector Assembly. It shows a prosthetic connector assembly for adjustably connecting a socket with a prosthetic limb includes an end plate having a top side, a bottom side, and a central opening therein. A socket extends upwardly from the top side of the end plate and an attachment member is supported on the bottom side thereof. An oblong washer is disposed within the socket and is supported by the top side of the end plate. A bolt extends through the attachment member, washer, and central opening in the end plate to retain the washer and attachment member against the end plate while permitting relative adjustment of the attachment member with respect to the end plate.

U.S. Pat. No. 5,888,233 to Randstrom is titled Arrangement for Leg Prosthesis. It shows that an adjustment head is provided to attach an elongated member of an artificial leg to a prosthetic leg. The adjustment head includes an upper portion and a lower portion. The upper portion provides adjustment of the elongated member in a translatory direction. The lower portion, in combination with the upper portion, provides adjustment of the elongated member in an angular direction. In making the translatory adjustment, the screw provided for this purpose will not be subject to direct breaking forces by being angled due to any angular adjustment of the elongated member, such screw always being maintained in a fixed vertical alignment.

U.S. Pat. No. 6,013,105 to Potts is titled Prostheses Connector and Alignment Assembly. It shows an apparatus and method for positioning and/or aligning a connector between a prosthetic socket and a prosthetic limb. An alignment assembly may have a rotational positioning module and a sliding adjustment unit to position a connector at a natural joint location for a particular patient. The connector may also independently rotate with respect to the sliding adjustment unit to align the connector faces with a set of natural articulation axes of the patient. After the components are positioned and aligned, the components may be fixed together to provide a fixed connector custom fitted to a particular patient.

U.S. Pat. No. 6,033,440 to Schall et al. is titled Adjustable Pyramidal Link Plate Assembly for a Prosthetic Limb. It shows that a pyramidal link-plate assembly for coupling a prosthetic limb upright assembly to another prosthetic limb component includes: a base plate member having a dome extending from a distal end and a cavity opening onto a distal apex of the dome, where the cavity includes a conically shaped portion with a diameter that widens with the distance from the distal apex of the dome; and a rotatable member which includes a substantially conically shaped body positioned within the conical portion of the cavity and which includes a frustopyramidal boss extending distally therefrom out through the opening in the distal apex of the dome. The conically shaped body of the rotatable member, positioned within the cavity, also widens with the distance from the distal apex of the dome. The boss is adapted to be received within a central opening of a conventional annular coupling-socket. Set screws that extend radially into the central opening of the coupling socket are angled slightly distally so that when the set screws abut the outwardly angled faces of the frustopyramidal boss, further tightening of the set screws acts to pull the boss component in the distal direction, thereby causing the outer conical surface of the rotatable member's conically shaped body to press against the inner conical surface of the cavity. Accordingly, when the set screws are tightened, surface friction between the two complementary conical surfaces prohibits further rotation of the rotatable member within the base plate member.

U.S. Pat. No. 6,231,618 to Schall et al. is titled Prosthetic Limb Including an Adjustable Pyramidal Link Plate Assembly. It shows that a pyramidal link-plate assembly for coupling a prosthetic limb upright assembly to another prosthetic limb component includes: a base plate member having a dome extending from a distal end and a cavity opening onto a distal apex of the dome, where the cavity includes a conically shaped portion with a diameter that widens with the distance from the distal apex of the dome; and a rotatable member which includes a substantially conically shaped body positioned within the conical portion of the cavity and which includes a frustopyramidal boss extending distally therefrom out through the opening in the distal apex of the dome. The conically shaped body of the rotatable member, positioned within the cavity, also widens with the distance from the distal apex of the dome. The boss is adapted to be received within a central opening of a conventional annular coupling-socket. Set screws that extend radially into the central opening of the coupling socket are angled slightly distally so that when the set screws abut the outwardly angled faces of the frustopyramidal boss, further tightening of the set screws acts to pull the boss component in the distal direction, thereby causing the outer conical surface of the rotatable member's conically shaped body to press against the inner conical surface of the cavity. Accordingly, when the set screws are tightened, surface friction between the two complementary conical surfaces prohibits further rotation of the rotatable member within the base plate member.

U.S. Pat. No. 7,166,132 to Callaway et al. is titled Adjustable Bone Prosthesis and Related Methods. It shows that an adjustable prostheses and related methods provide a wide range of adjustment along or about multiple axes. The prostheses and related methods make possible a straightforward, yet robust way of securing, e.g., a humeral head prosthesis in a desired position and maintaining the prosthesis in the desired position during use.

U.S. Pat. No. 7,338,532 to Haberman et al. is titled Alignment Assembly for a Prosthesis. It shows an alignment assembly for a modular prosthesis. The alignment assembly includes a plurality of modular components that can be selectively connected to each other for providing selectively linear adjustability along first and second non-parallel axes, and rotational/angular adjustability about three orthogonal axes.

United States Publication Number 2004/0059433 to Slemker et al. is titled Prosthetic Knee-Joint Assembly Including Adjustable Proximal and/or Distal Couplings. It shows that a prosthetic knee-joint assembly includes: (a) a proximal segment; (b) a distal segment pivotally disposed with respect to the proximal segment to form a knee joint; (c) a first coupling integral with the proximal segment that includes a first adjustable member having a frustopyramidal boss extending proximally with respect to the proximal segment that is adapted to mount the proximal segment to above-knee prosthetic knee components, where the frustopyramidal boss is slidably adjustable and/or rotatably adjustable with respect to the proximal segment; and (d) a second coupling integral with the distal segment that includes a second adjustable member having a second frustopyramidal boss extending distally with respect to the distal segment that is adapted to mount the distal segment to below-knee prosthetic limb components, and where the second frustopyramidal boss is slidably adjustable and/or rotatably adjustable with respect to the distal segment.

United States Publication Number 2005/0027371 to Chen is titled Artificial Limb with Relative Position-Adjustable Upper and Lower Limb Parts. It shows an artificial limb includes a prosthetic upper limb part, a prosthetic lower limb part, an upper connecting piece disposed under and connected fixedly to the upper limb part, a lower connecting piece disposed under the upper connecting piece and disposed over and connected fixedly to the lower limb part, and a locking member for locking the upper and lower connecting pieces releaseably on each other. The locking member is operable to permit relative movement of the upper and lower connecting pieces in a transverse direction of the artificial limb in such a manner that the upper and lower connecting pieces are retained on the locking member.

United States Publication Number 2014/0074254 to Curtis is titled Laterally and Rotatably Adjustable Alignment Device with Optional Scales and Secure Connections. It shows an invention that relates to an offset alignment device with a longitudinal axis that is capable of singularly offsetting two prosthetic components a selected distance along an alignment axis that is selectably oriented in a plane that is generally perpendicular to the longitudinal axis, and is also capable of adjusting the rotational orientation between the two prosthetic components that are connected to the present invention about a rotational axis. This is accomplished by providing a first member having an end comprising a channel. A second member is also provided having a crown for being laterally adjustably connected to the first member along an alignment axis and also rotationally adjustably connected to the first member along a rotational axis. In an alternative embodiment, scales are provided for measuring the adjustments made to the device.

None of the devices shown in these patents and publications show the present invention.

Thus there exists a need for a prosthetic device having a rotatable pyramid and lateral travel limit that solves these and other problems.

SUMMARY OF THE INVENTION

A prosthetic device having a rotatable pyramid and lateral travel limit is provided. A first member has a first end connectable to a prosthetic component and a second end with a bar having sides and a distal face. The distal face has ribs thereon. A central hole is provided through the first member. A second member has a first end with a pyramid and a second end with a ring that defines a recess with a solid face. A third member has a dome on a first end and a channel on the second end. The pyramid extends through a central hole through the dome. A screw passes through the central hole of the first member wherein it can engage the second member within the recess. The lateral movement of the bar within the channel is bound by the screw contacting the second member.

According to one advantage of the present invention, a bar of a first member is provided for laterally sliding within a channel of a third member to provide a desired offset between the two members. Ribs can be provided on the bar, wherein screws inserted through the third member engage ribs on the bar to laterally lock the members in place.

According to a further advantage of the present invention, a travel limit is provided to define the maximum offset distance between the members of the device.

In the illustrated embodiment, the travel limit is integrated in the second member. Specifically, the second end of the second member has a ring protruding from the sidewall. The ring defines a recess having a diameter which defines the travel limit relative to the first and third members.

The pyramid of the second member is rotatable relative to the third member. Yet, advantageously, the limit or range of lateral travel between the first and third members is unchanged regardless of the rotational orientation of the second member. This is accomplished as the recess is generally circular shaped in profile whereby the diameter of the circle can define the maximum travel of the first member relative to the third member.

According to a further advantage of the present invention, the recess can have a solid face. This advantageously could allow a screw or other structure to make solid contact with the face within the entirety of the recess.

According to a further advantage of the present invention, the device is compact.

According to a still further advantage of the present invention, the screw that cooperates with the ring is concealed when the device is connected to other prosthetic components. This advantageously prevents the screw from being damaged or unintentionally removed or loosened.

Other advantages, benefits, and features of the present invention will become apparent to those skilled in the art upon reading the detailed description of the invention and studying the drawings.

BRIEF DESCRIPTION OF THE DRAWINGS

FIG. 19 is an alternative perspective view of the second member.

FIG. 20 is a side view of the second member.

FIG. 21 is an end view of the second member.

FIG. 24 is an isolated side view of the third member of the present invention.

FIG. 25 is an end view of the third member.

FIG. 26 is a perspective view of the third member.

DETAILED DESCRIPTION OF PREFERRED EMBODIMENTS

While the invention will be described in connection with one or more preferred embodiments, it will be understood that it is not intended to limit the invention to those embodiments. On the contrary, it is intended to cover all alternatives, modifications and equivalents as may be included within the spirit and scope of the invention as defined by the appended claims.

Figure 1:
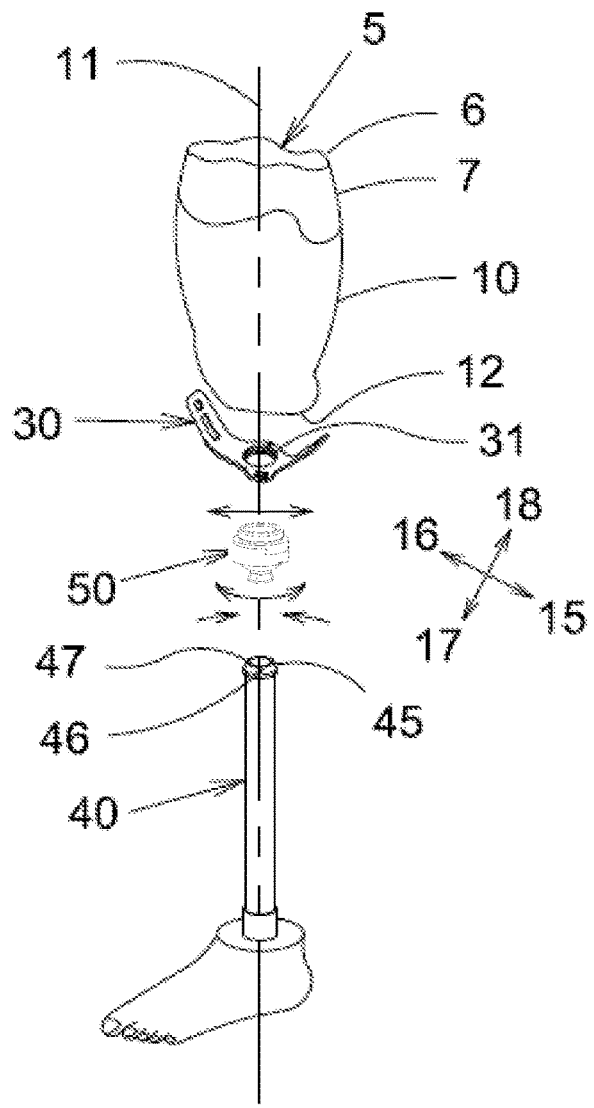
FIG. 1 is an exploded perspective view of the device of the present invention in relation with adjacent items.
Figure 2:
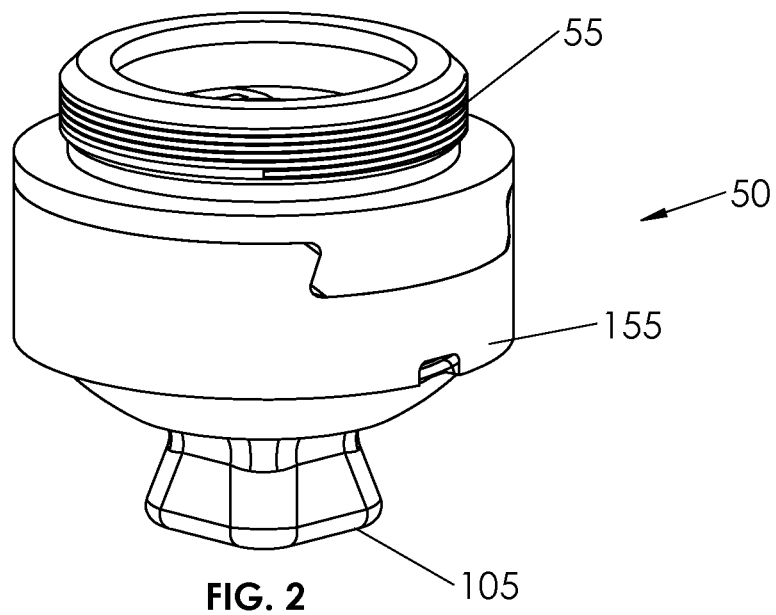
FIG. 2 is a perspective view of a preferred embodiment of the present invention.
Figure 3:
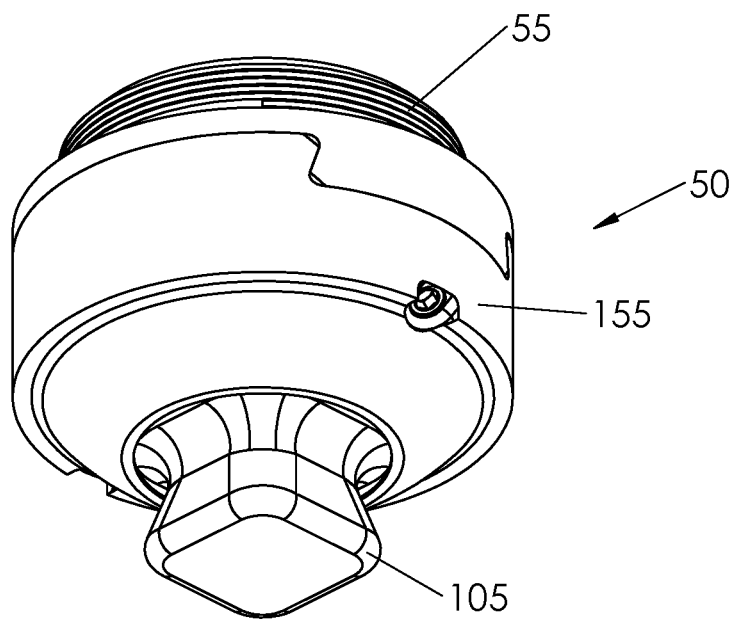
FIG. 3 is an opposite perspective view of the preferred embodiment of the present invention as illustrated in FIG. 2.
Figure 4:
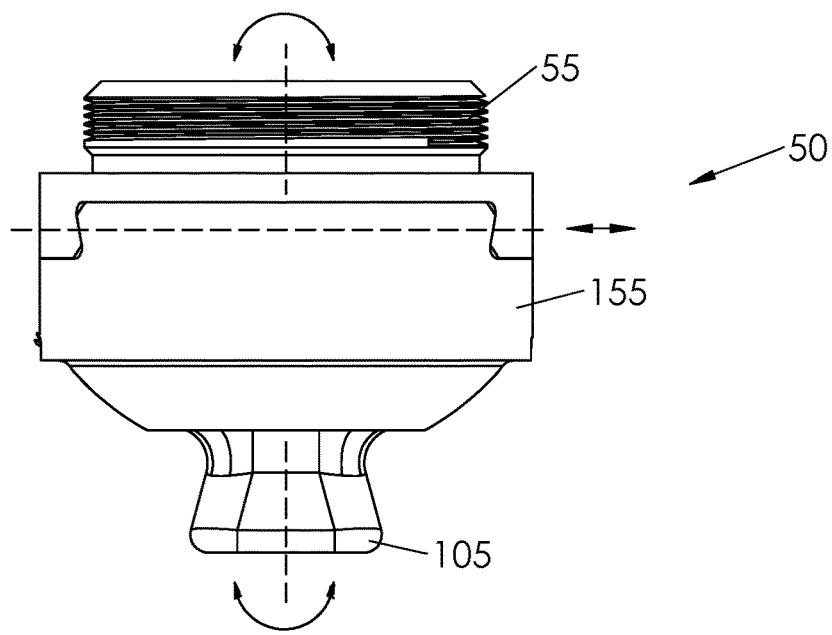
FIG. 4 is a side view of the preferred embodiment of the present invention as illustrated in FIG. 2.
Figure 5:
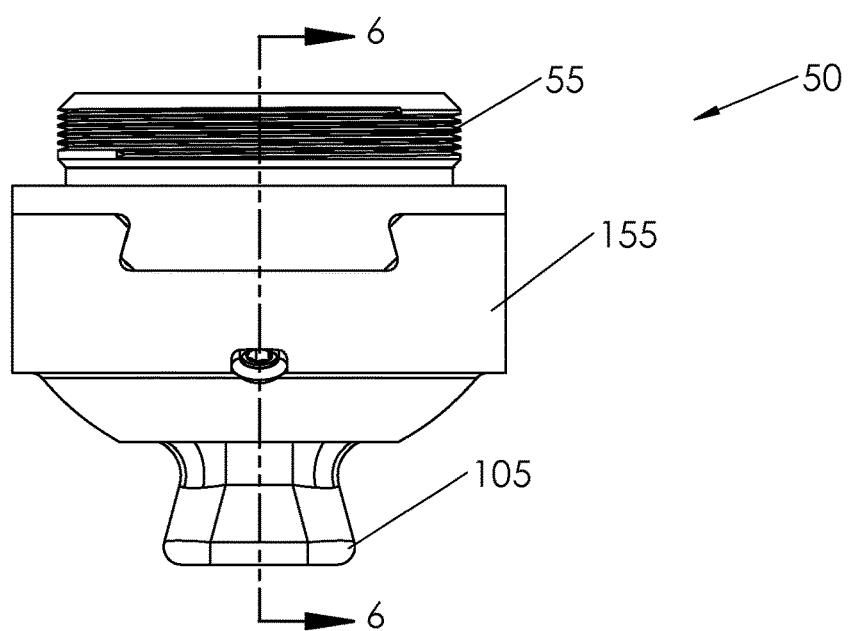
FIG. 5 is an alternative side view of the preferred embodiment of the present invention as illustrated in FIG. 2.
Figure 6:
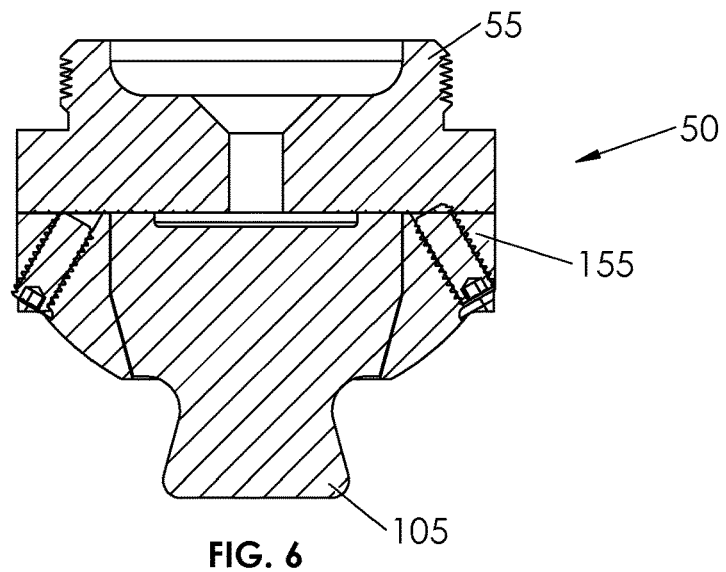
FIG. 6 is a cross-sectional view taken along line 6-6 in FIG. 5.
Figure 7:
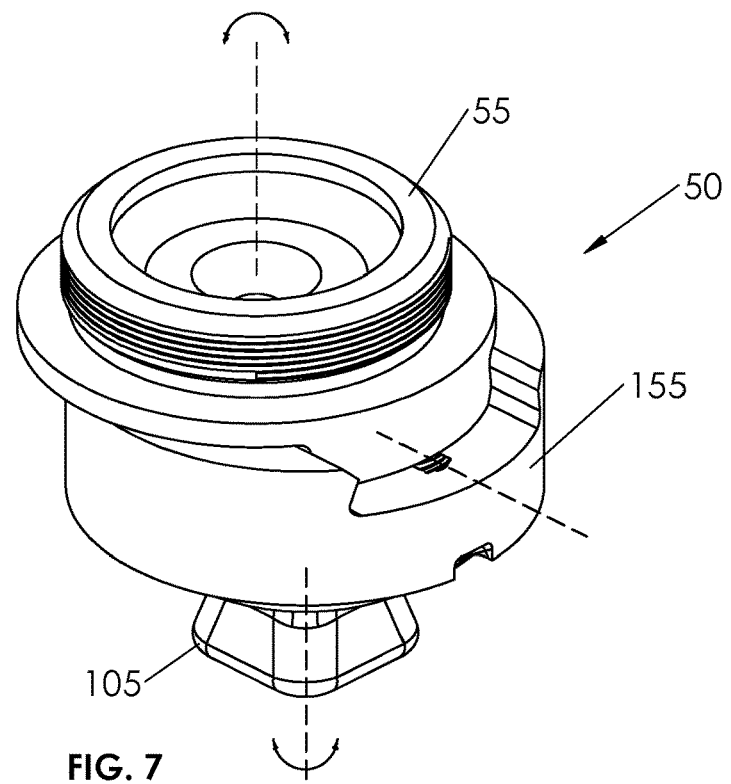
FIG. 7 is a perspective view showing the third member laterally offset from the first member.
Figure 8:
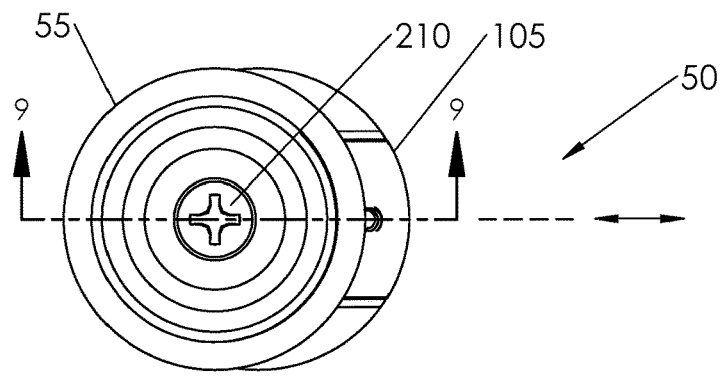
FIG. 8 is a top view of FIG. 7
Figure 9:
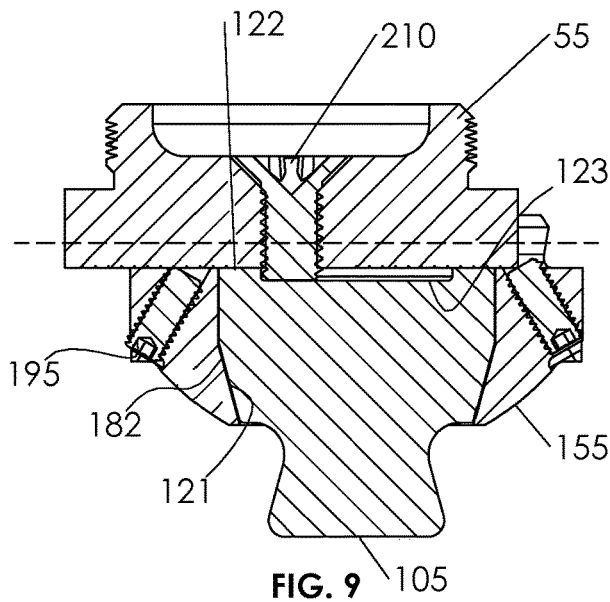
FIG. 9 is a cross-sectional view taken along line 9-9 in FIG. 8.
Figure 10:
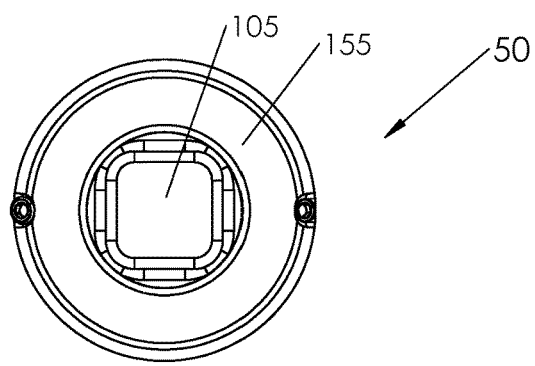
FIG. 10 is an end view of the preferred embodiment of the present invention as illustrated in FIG. 2.
Figure 11:
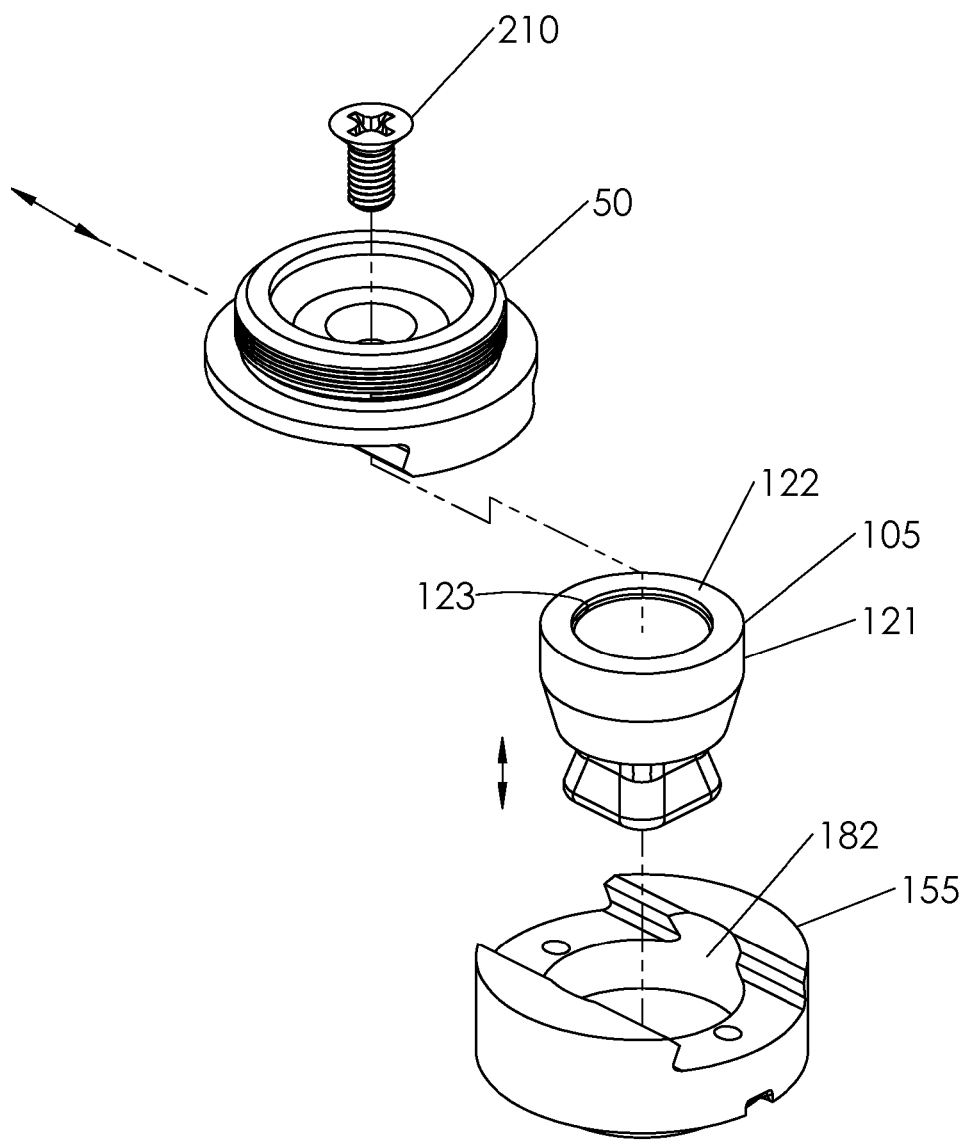
FIG. 11 is an exploded view of the preferred embodiment of the present invention as illustrated in FIG. 2.
Figure 12:
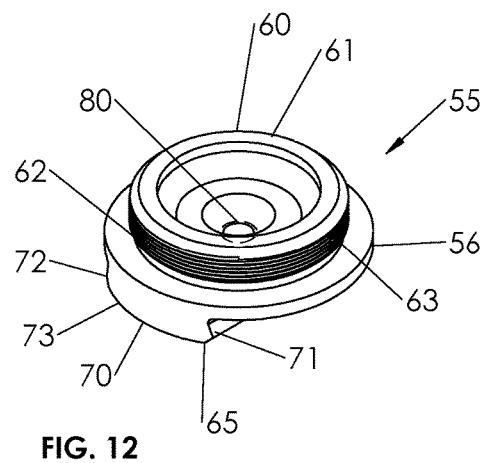
FIG. 12 is an isolated perspective view of a first member of the present invention.
Figure 13:
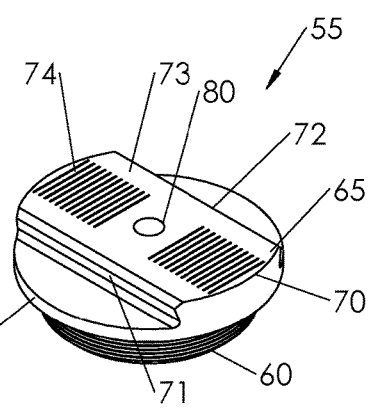
FIG. 13 is an alternative perspective view of the first member.
Figure 14:
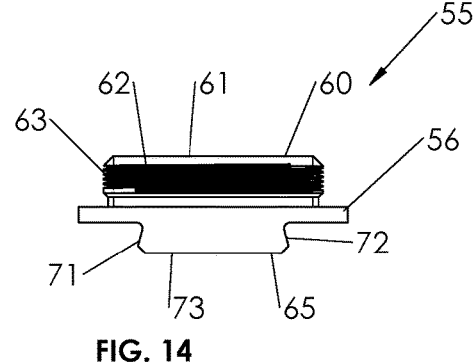
FIG. 14 is a side view of the first member.
Figure 15:
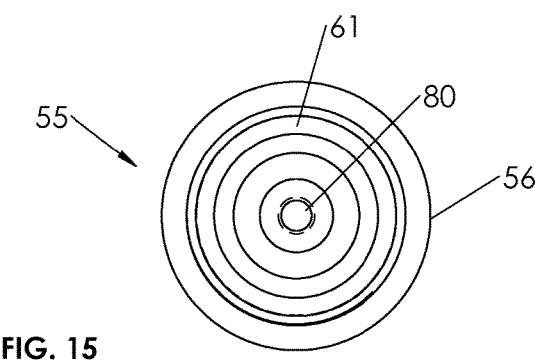
FIG. 15 is an end view of the first member.
Figure 16:
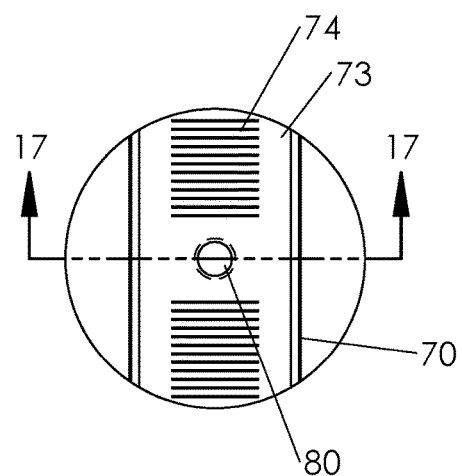
FIG. 16 is an alternative end view of the first member.
Figure 17:
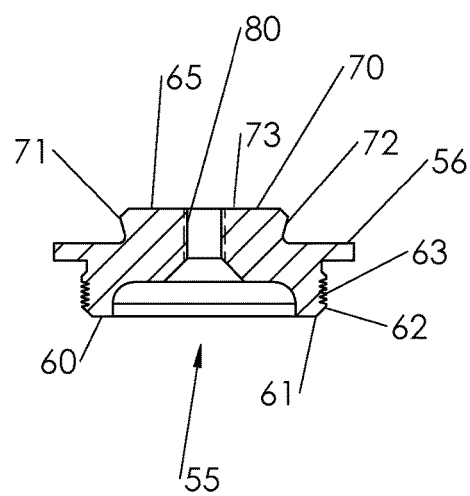
FIG. 17 is a cross-sectional view taken along line 17-17 in FIG. 16.
Figure 18:
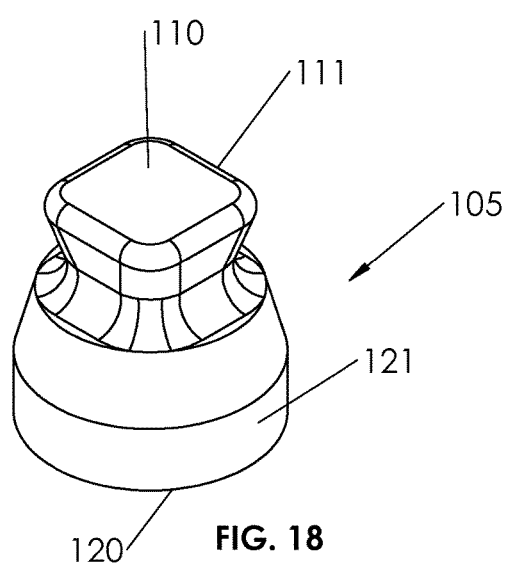
FIG. 18 is an isolated perspective view of the second member of the present invention.
Figure 22:
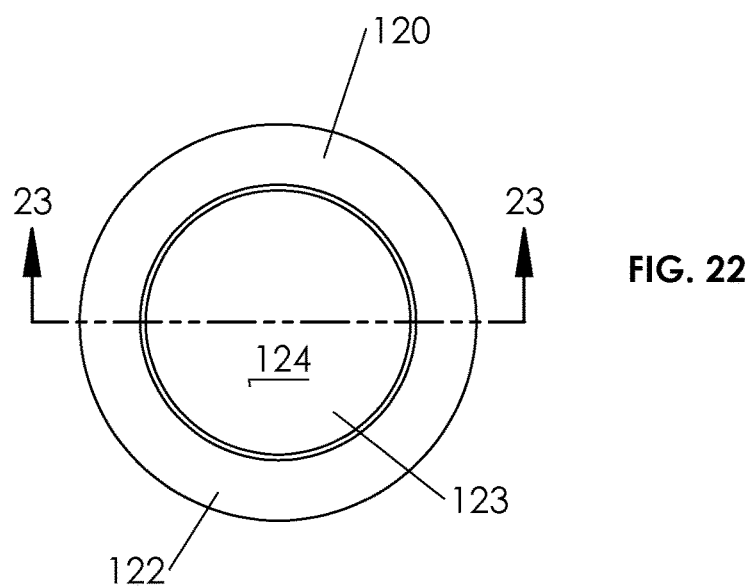
FIG. 22 is an alternative end view of the second member.
Figure 23:
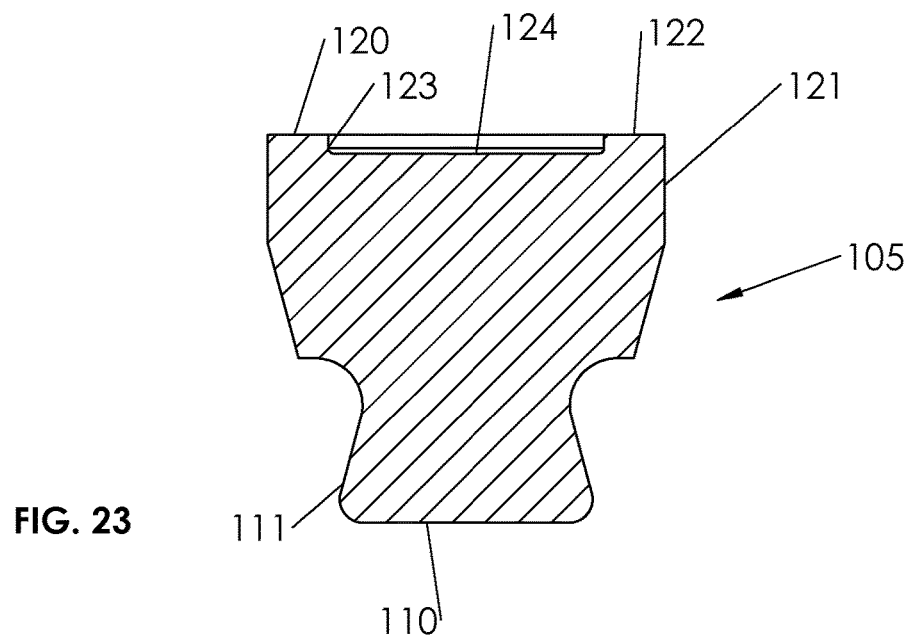
FIG. 23 is a cross-sectional view taken along line 23-23 in FIG. 22.
Figure 27:
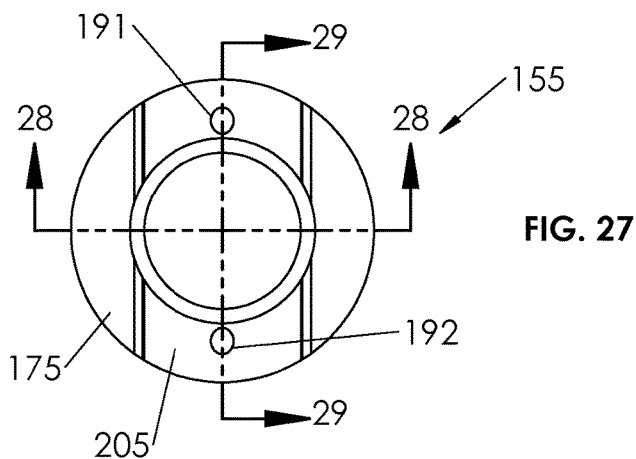
FIG. 27 is an alternative end view of the third member.
Figure 28:
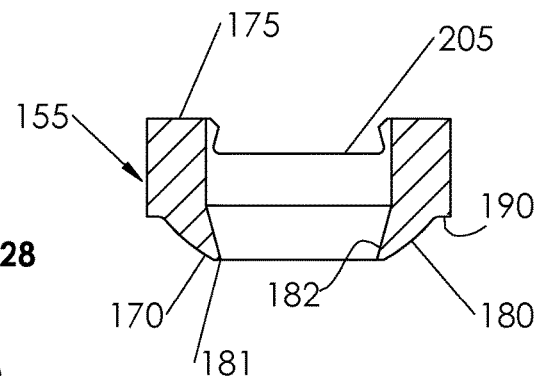
FIG. 28 is a cross-sectional view taken along line 28-28 in FIG. 27.
Figure 29:
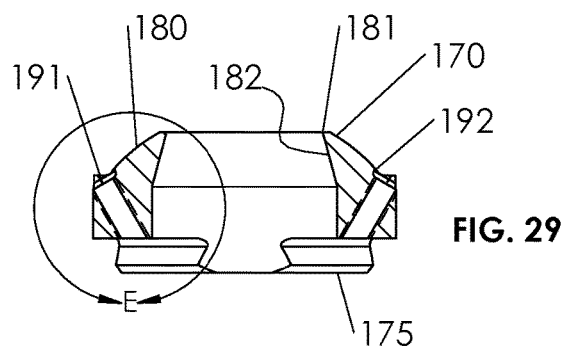
FIG. 29 is a cross-sectional view taken along line 29-29 in FIG. 27.
Figure 30:
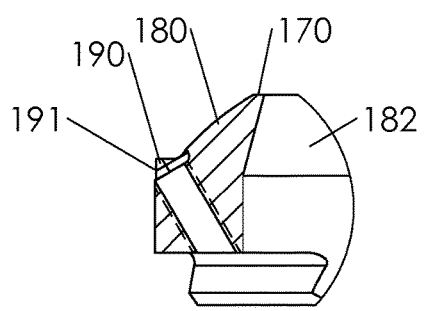
FIG. 30 is an enlarged view of a portion of FIG. 29.

Looking first to FIG. 1, it is seen that a possible environment for use of the present invention is illustrated. A person 5 having a limb 6 terminating in a stump 7 is provided. A socket 10 with a socket central axis 11 and an end 12 is further provided. A three prong adapter 30 with a threaded clamp 31 is further provided. The three prong adapter is connectable to the end 12 of the socket 10. A pylon 40 is further provided having a four-hole clamp 45 with holes 46 and a rim 47. It is appreciated that while certain ancillary components are illustrated, that the present invention is not limited for use with those components.

A device 50 of the present invention is useful to overcome offset between the pylon 40 and the socket central axis 11 in the lateral direction 15, medial direction 16, anterior direction 17, posterior direction 18 or some combination thereof.

The device 50 is illustrated in FIGS. 2-30. The device 50 can be made of any suitable material, including but not being limited to metal, steel, titanium alloy, aluminum or other materials. The device 50 has a first member (or piece) 55, a second member (or piece) 105 and a third member (or piece) 155. Each of these components is described below.

The first member 55 is illustrated in isolated views in FIGS. 12-17. The first member 55 has a center (or central portion) 56. A first end 60 is provided having a connector 61. The connector 61 has an exterior surface 62 threaded with threads 63. A second end 65 is also provided. The second end 65 has a bar 70. Bar 70 is formed of two sides 71 and 72 and a distal face 73. The sides 71 and 72 preferably diverge from each other moving away from the center 56. Each side 71 and 72 has an outer edge where the sides meet the distal face 73. These edges are preferably generally parallel to each other. A plurality of ribs (or teeth or protrusions) 74 are oriented across the face 73 between the sides 71 and 72. The ribs 74 are preferably generally parallel to each other. A central hole 80 is provided and passes through the first member 55. The central hole 80 preferably passes through the geometric center of the bar 70 and is aligned generally perpendicular to the distal face 73. The central hole 80 is preferably threaded and can threadably receive screw 210.

Turning now to FIGS. 18-23, it is seen that the second member 105 is illustrated in isolated views. The second member 105 has a first end 110 with a pyramid 111 formed thereon. The second member 105 further has a second end 120 with a sidewall 121. Sidewall 121 preferably has a generally circular shaped profile. Sidewall 121 has a cone-shaped (angled) portion and a constant diameter portion. A ring 122 extends from the end of sidewall 121. The ring has a generally circular shaped interior perimeter. The ring 122 defines a recess 123 with a solid interior face 124. That is, face 124 preferably has no holes there through. Further, face 124 is preferably flat.

Turning now to FIGS. 24-30, it is seen that the third member 155 of the device 50 is illustrated in isolated views. The third member 155 has two opposed ends 170 and 175, respectively. A dome 180 having a central hole 181 and a sidewall 182 is provided on the first end 170. The central hole has an angled portion and a constant diameter portion. The sidewall 182 terminates at a platform 190. The platform 190 has a generally circular shaped profile. Two angled holes 191 and 192 are formed through the platform. The holes 191 and 192 are preferably located about 180 degrees from each other. A sidewall 200 is at the second end 175 of the third member 155. A channel 205 is formed into the second end 175 and is open through the sidewall 200 on both sides of the third member. The channel is shaped for mating engagement with the bar 70 of the first member 55. In this regard, the channel 205 has sidewalls that respectively are angled towards each other as they span towards the end 175 of the member 155. The channel 205 further has a base face. The two screw holes 191 and 192 both pass into the channel 205 and are located at opposite sides of the channel. Screws 195 can be received through holes 191 and 192.

Looking now at FIGS. 2-11, the assembly and use of device 50 is explained including positioning and orientation of the three members 55, 105 and 155.

The second member 105 is received within the third member 155. Specifically, the first end 110 is received within the central hole 181 of the third member by being inserted from end 175 wherein the pyramid 111 extends beyond the dome 180. The angled portion of sidewall 121 mates with the angled portion of hole 181 to prevent the second member 105 from passing completely through the central hole 181. The second member 105 is rotatable about an axis relative to the third member 155 so that the rotational orientation of the pyramid can be adjusted. The second piece is frictionally held in tight engagement with the third piece when adjacent prosthetic components are connected to the pyramid and press against the dome.

The bar 70 of the first member is laterally and adjustably received within the channel 205 of the third member 155. The second member 105 cannot be removed from the third member 155 when the first member 55 is slid into the third member 155. Screw 210 can be inserted into the central hole 80 of the first member wherein it can be placed against or adjacent to the face 124 of the recess 123 of the second member 105. In this regard, the screw 210 distal end is within the perimeter of the ring 122. Screw 210 can accordingly be called a lock screw. The lateral travel of the first member 55 relative to the third member 155 is limited by the distance that the ring 122 can travel before it contacts the screw 210. It is appreciated that the amount of the first member 55 relative to the third member 155 is unchanged by the rotational orientation of the second member 105 relative to the third member 155.

The first member 55 can be removed from the third member 155 when the screw 210 is unthreaded a sufficient amount wherein the distal end of the screw would not engage the ring 122 when the pieces are laterally moved relative to each other and the screw would not be capable of engaging the ring. The pyramid is removable from the third member when the first member and third member are disengaged.

Screw 210 can, but does not need to, engage the bottom surface 124 of the second end 120 of the second member 105. In embodiments where the screw contacts the solid face 124, the force of the screw reinforces the pressing of the sidewall 121 against the side wall 182 of the central hole 181 of the dome 180 of the third member 155.

It is appreciated that while a screw 210 is illustrated, that a pin or other type of limiter could be used without departing from the broad aspects of the present invention.

Screws 195 can be inserted into holes 191 and 192 wherein they enter channel 205 to contact ribs 74 of the bar 70. Holes 191 and 192 are preferably angled inwards. Engagement between the screws and ribs creates a stable connection between the two members to lock the lateral offset position on the device in place (specifically the lateral position of the first member relative to the third member). Accordingly, screws 195 can be called lock screws.

Thus, it is apparent that there has been provided, in accordance with the invention, prosthetic device having a rotatable pyramid and lateral travel limit that fully satisfies the objects, aims and advantages as set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

We claim:

1. A device comprising:
   a first member with a bar and a central hole, said central hole receiving a limiter;
   a second member having a ring with a diameter; and
   a third member with a channel and a tapered hole, said bar being laterally movably received within said channel and said second member being received within said tapered hole, said third member being laterally adjustable relative to said first member by a distance that is no greater than said diameter of said ring as said limiter contacts said ring at outer travel limits preventing additional lateral travel of said bar relative to said channel.

2. The device of claim 1 wherein said first member comprises:
   a first member first end with a connector; and
   a first member second end with said bar.

3. The device of claim 1 wherein said bar has a plurality of ribs thereon.

4. The device of claim 3 wherein a lock screw passes through said third member contacts one of said plurality of ribs to lock said third member relative to said first member.

5. The device of claim 1 wherein said second member comprises:
   a second member first end with a pyramid; and
   a second member second end, said ring being at said second member second end.

6. The device of claim 5 wherein said third member comprises a dome.

7. The device of claim 6 wherein:
   said second member has an angled side wall between said pyramid and said ring, said pyramid extending from said dome when said angled side wall engages said tapered hole.

8. The device of claim 1 wherein said second member is rotatable within said tapered hole to a rotational position, yet a travel range between said first member and said third member is unchanged regardless of said rotational position.

9. A device comprising:
   a first member having a bar and a central hole;
   a second member having a pyramid and a ring, said ring having a ring interior defining a ring diameter, said ring having a recess having a solid face;
   a third member having a channel; and
   a limiter insertable through said first member into said recess so that movement of said bar relative to said channel is limited as said limiter is bound by said ring, wherein:
      said pyramid is rotatable relative to said third member to a rotational position;
      said bar is adjustably received within said channel in a lateral direction;
      lateral movement of said bar relative to said channel is limited to a maximum lateral travel wherein said limiter contacts said ring, said maximum lateral travel being unrelated to said rotational position of said pyramid.

10. The device of claim 9 wherein said limiter is a limit screw.

11. The device of claim 10 wherein at least one lock screw can pass through said third member to contact said first member to lock said third member in a lateral position relative to said first member.

* * * * *